(12) United States Patent
Alexeev

(10) Patent No.: US 12,178,730 B2
(45) Date of Patent: Dec. 31, 2024

(54) FLEXION BLOCKING ELBOW BRACE FOR CUBITAL TUNNEL TREATMENT

(71) Applicant: Mikhail Alexeev, Lexington, SC (US)

(72) Inventor: Mikhail Alexeev, Lexington, SC (US)

(*) Notice: Subject to any disclaimer, the term of this patent is extended or adjusted under 35 U.S.C. 154(b) by 438 days.

(21) Appl. No.: 17/390,449

(22) Filed: Jul. 30, 2021

(65) Prior Publication Data

US 2023/0010951 A1  Jan. 12, 2023

Related U.S. Application Data

(60) Provisional application No. 63/220,055, filed on Jul. 9, 2021.

(51) Int. Cl.
*A61F 5/01* (2006.01)

(52) U.S. Cl.
CPC ............ *A61F 5/0118* (2013.01); *A61F 5/012* (2013.01); *A61F 2005/0165* (2013.01)

(58) Field of Classification Search
CPC ........ A61F 5/0118; A61F 5/012; A61F 5/013; A61F 2005/0165
See application file for complete search history.

(56) References Cited

U.S. PATENT DOCUMENTS

| | | | | |
|---|---|---|---|---|
| 5,514,081 A | * | 5/1996 | Mann | A61F 5/013 128/DIG. 20 |
| 7,841,997 B1 | * | 11/2010 | Heller | A61F 5/3738 128/878 |
| 8,366,647 B2 | * | 2/2013 | Murinson | A61F 5/0118 602/61 |
| 8,460,226 B2 | * | 6/2013 | Rushton | A61F 5/019 602/30 |
| 10,315,088 B2 | * | 6/2019 | Hall | A63B 69/0002 |
| 2014/0155795 A1 | * | 6/2014 | Evenden | A61F 5/012 602/13 |
| 2017/0065448 A1 | * | 3/2017 | Michell | A61F 5/0118 |

* cited by examiner

*Primary Examiner* — Keri J Nelson
(74) *Attorney, Agent, or Firm* — William D. Hare; McNeely & Hare, LLP

(57) ABSTRACT

The invention relates to a brace comprising: (i) a distal mounting portion comprising a first loop configured to enclose a portion of an arm of a patient wearing the brace; (ii) a proximal mounting portion comprising a second loop configured to enclose a portion of the arm of the patient wearing the brace; and (iii) a body portion positioned between, and connected to, the distal mounting portion and the proximal mounting portion. The body portion includes at least two layers defining a pouch region between the two layers and configured to receive an object.

16 Claims, 4 Drawing Sheets

FLEXION BLOCKING ELBOW BRACE FOR CUBITAL TUNNEL TREATMENT

TECHNICAL FIELD

The technical field of the invention relates to a medical device for treating cubital tunnel syndrome resulting from ulnar nerve compression at the elbow.

BACKGROUND

Cubital tunnel syndrome is a medical condition which is caused by ulnar nerve compression at the elbow, and is the second most common compressive neuropathy of the upper extremity. The ulnar nerve provides sensation to the small and ring fingers of the hand, as well as motor supply to many of the muscles within the hand. Chronic nerve compression and irritation results in slowing of the electrical signal transmitted through the nerve, which can result in detrimental effects on the function of the hand and upper extremity. Patients suffering from cubital tunnel syndrome may present with numbness in the small and ring fingers, hand clumsiness and weakness caused by muscle atrophy resulting from chronic ulnar nerve compression, and in some cases, sensitivity and painful irritation of the ulnar nerve at the elbow. Cubital tunnel syndrome treatments may vary based on the severity and chronicity of the disease. In most cases, patients are first treated conservatively with avoidance of symptom-provoking activity, bracing, and anti-inflammatory medications. Patients who fail conservative management typically undergo surgical release of the cubital tunnel to remove any anatomic sites of nerve compression.

SUMMARY

In a first aspect, the invention relates to a brace comprising: (i) a distal mounting portion comprising a first loop configured to enclose a portion of an arm of a patient wearing the brace; (ii) a proximal mounting portion comprising a second loop configured to enclose a portion of the arm of the patient wearing the brace; and (iii) a body portion positioned between, and connected to, the distal mounting portion and the proximal mounting portion. The body portion includes at least two layers defining a pouch region between the two layers and configured to receive an object.

Embodiments of the brace may include one or more of the following features. For example, the brace further comprises an object sized to fit within the pouch region. The object may have the shape of a ball. The ball may be inflatable. The object may have the shape of a cylinder.

The brace may further include multiple objects sized to fit within the pouch region. At least two of the multiple objects may have different diameters.

The distal mounting portion may include a first fastener to attach a portion of the first loop to the distal mounting portion and the proximal mounting portion may include a second fastener to attach a portion of the second loop to the proximal mounting portion. Each fastener may include a hook-and-loop fastener strip.

In one embodiment, the pouch region may include four sides and three of the four sides have the two layers being attached. The fourth of the four sides may include a hook-and-loop fastener to attach the two layers or a button or snap to attach the two layers. The fourth of the four sides may include an elastic strip to reduce the size of the opening into the pouch.

In another embodiment, the pouch region may include four sides and two of the four sides have the two layers being attached. Two of the four sides are not attached and each includes an elastic strip to reduce the size of the opening into the pouch.

In another embodiment, the first loop comprises an elastic sleeve and the second loop comprises an elastic sleeve.

In another general aspect, the invention relates to a method of treating cubital tunnel syndrome resulting from ulnar nerve compression at the elbow. The method includes positioning a brace as described herein on an arm of a patient with the first loop of the distal mounting portion placed around a distal portion of the arm distal to the elbow and the second loop of the proximal mounting portion placed around a proximal portion of the arm proximal to the elbow; and inserting an object into the pouch of the brace, wherein the object limits flexion of the arm.

Embodiments of the method of treatment may include one or more of the following features or those described above. For example, the object may have the shape of a ball or a cylinder. The ball or cylinder may be inflatable.

The method may further include providing at least two objects of different sizes and exchanging a first object for a second object within the pouch.

DETAILED DESCRIPTION

Braces used for the treatment of cubital tunnel syndrome can aim to relieve symptoms in various ways. One method of treating cubital tunnel syndrome is by minimizing the ability to flex the elbow, thereby minimizing the amount of nerve compression which occurs in that area. It has been demonstrated in the orthopedic literature that the volume of the cubital tunnel decreases with elbow flexion past 90 degrees. A decrease in the available space in the cubital tunnel increases ulnar nerve compression and produces symptoms of cubital tunnel syndrome. Activities involving repetitive elbow flexion my provoke the onset of symptoms, and patients often suffer from symptoms of cubital tunnel at night due to the tendency of many individuals to sleep with the elbow held in a high degree of flexion. Prolonged elbow flexion at night results in compression and ischemia of the nerve, causing nerve irritation and often results in worsening day-time symptoms. Current brace technologies have attempted to minimize elbow flexion, however the currently available devices are either too bulky or too restrictive, preventing the patient from being able to range the elbow in a safe range of motion (0-90 degrees of elbow flexion). This leads to poor patient compliance with night time bracing and likely results in many failed cases of non-operative management of cubital tunnel syndrome. The inventor has developed an elbow brace which treats cubital tunnel by preventing the extremes of elbow flexion but likewise allowing for unrestricted elbow range of motion within lesser degrees of flexion. The brace will consist of a flexion blocking device placed within a pouch of the brace, which will then be placed in the antecubital fossa of the affected arm of the patient and secured in place with two elastic straps, thereby providing a block to high degrees of elbow flexion.

Figure 1:
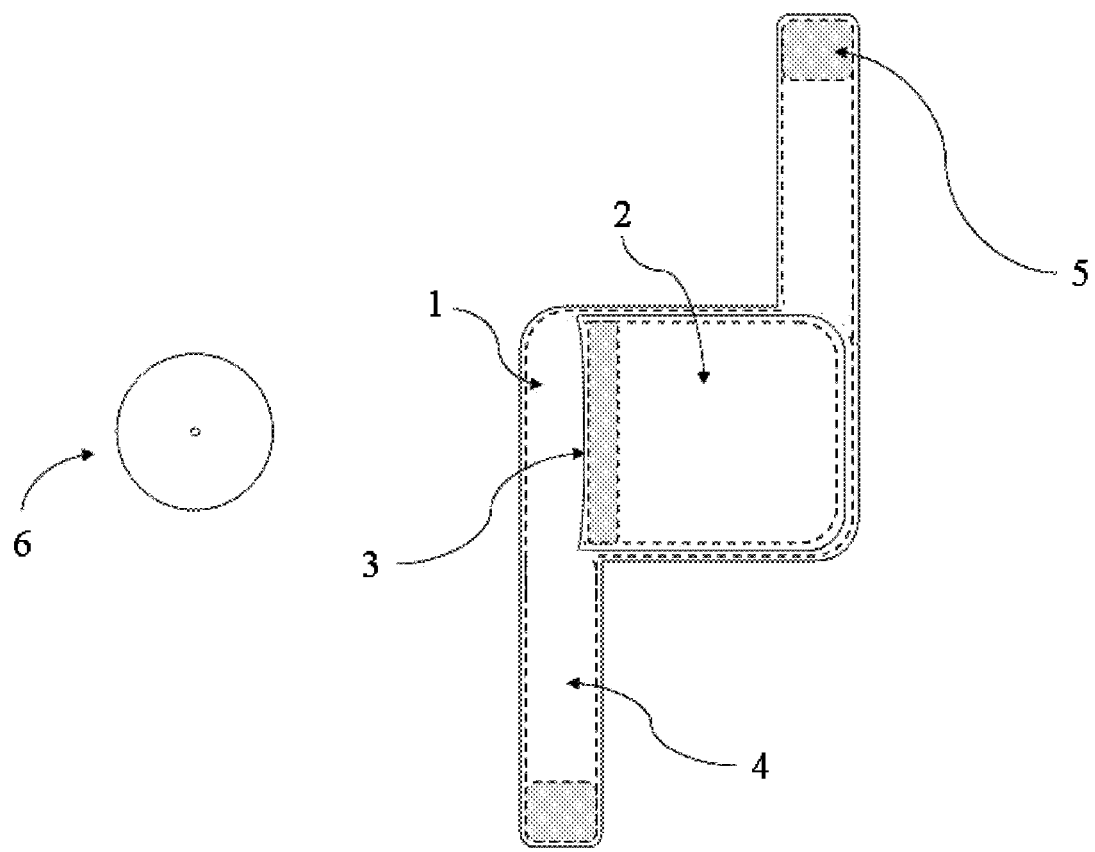
FIG. 1 is a bottom view of the flexion blocking elbow brace with an inflatable ball.
Figure 2:
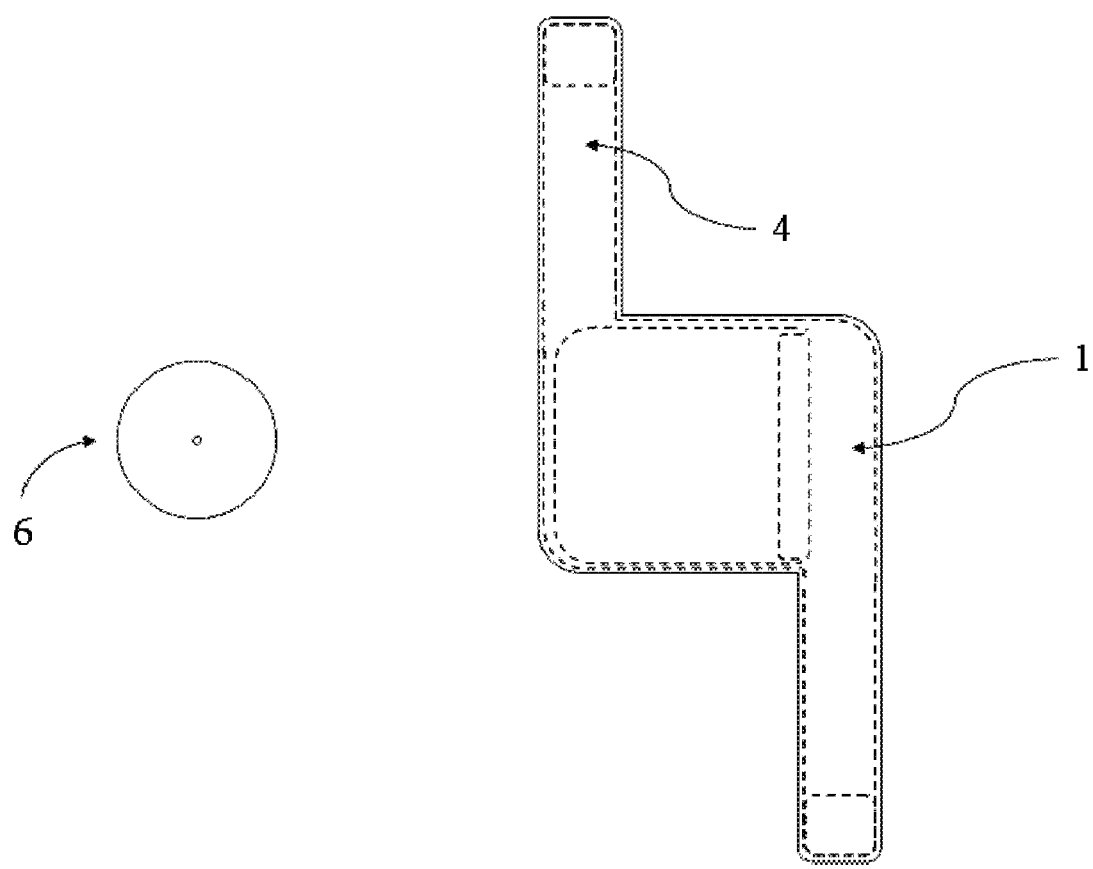
FIG. 2 is a top view of the flexion blocking elbow brace with the inflatable ball.
Figure 3:
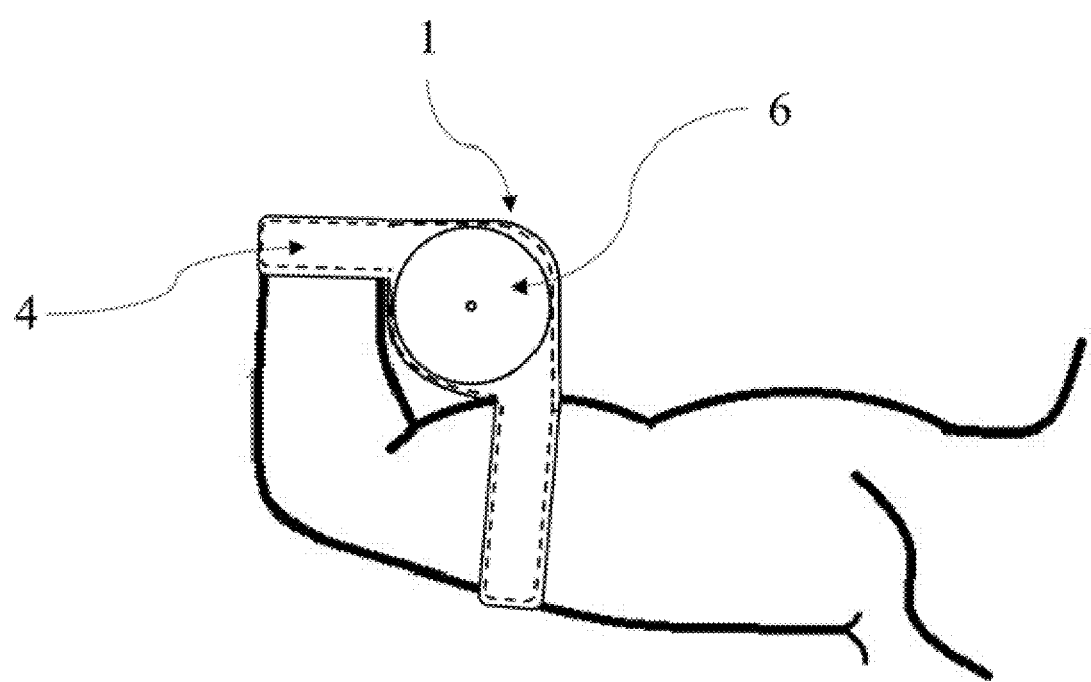
FIG. 3 is a side view of flexion blocking elbow brace with the inflatable ball placed within the pouch and applied to the right upper extremity with the bottom side of the brace facing the antecubital fossa.

FIGS. 1-3 demonstrate the components of the brace, as described below in more detail. The brace includes a body 1, a ball pouch 2, an opening 3 into the pouch 2, a pair of proximal and distal brace straps 4, and a pair of fastener strips 5. A ball 6 or other suitable article is placed within the pouch to limit flexion.

Component 1 demonstrates the body of the brace. The body 1 of the brace can be manufactured in an unlimited number of geometric configurations, with the depicted example demonstrating a modified Z shape consisting of two 90 degree angles. The brace will be composed of a central portion of fabric with thinner fabric pieces, or straps, protruding either perpendicularly or at an angle from the main body of the brace both medially and laterally from the proximal and distal ends, respectively. The perfectly symmetric shape of the brace will allow for it to be rotated 180 degrees if the patient desires to have the opening for the hook-and-loop fastener (Velcro) enclosed ball pouch to face toward or away from their body. The brace will be constructed from a light weight, breathable, elastic fabric which will aim to maximize patient comfort. Examples of materials which could be utilized to construct the brace include cotton, polyester, nylon, or combinations of those or other similar materials.

Component 2 demonstrates the hook-and-loop fastener enclosed ball pouch. This pouch serves as a location to place a solid or inflatable ball (or other flexion blocking object) which will be utilized as the primary block to elbow flexion. The pouch will be large enough to accommodate the ball, but not so large as to allow for excessive ball motion within the pouch. The pouch will be positioned on the interior of the brace, and placed directly onto the antecubital fossa of the patient. The pouch will be constructed of a durable, breathable material which will maximize the longevity of the pouch while maintaining maximum patient comfort. Examples of materials which could be utilized to construct the pouch include cotton, polyester, nylon, or combinations of those or other similar materials. Three sides of the pouch will be sewn into the body of the brace, while the most distal aspect of the pouch will serve as the location for the hook-and-loop fastener pouch opening.

In an alternative embodiment, the pouch can be formed with two sides of the pouch sewn or attached into the body of the brace and thereby forming two openings into the pouch. In this manner a ball or other article can be inserted from either opening.

Component 3 demonstrates the hook-and-loop fastener opening for the ball pouch. This opening will allow for easy insertion of the inflatable flexion blocking ball (component 6) or other flexion blocking object of the patient's choosing. The hook-and-loop fastener lining the opening of the ball pouch will prevent the contents of the pouch from exiting once they are placed within the pouch. The hook-and-loop fastener will be sewn to the most distal portion of the pouch in such a manner that it is completely concealed under the fabric of the pouch, minimizing any patient discomfort from the hook-and-loop fastener material. A button, zipper, or other fastening technology may also be utilized to provide a secure enclosure for the pouch.

In an alternative embodiment, the fastening technology can be in the form of an elastic strip that tends to reduce the size of the opening or openings into the pouch. In this manner a ball or other article can be inserted into the opening by stretching the elastic strip to enlarge the opening and then releasing the opening to reduce the size of the opening and retain the ball or other article within the pouch.

Components labeled 4 demonstrate the brace straps, which will protrude from the proximal and distal ends of the body of the brace, and in this example are positioned perpendicular to the axis of the patient's extremity, although various configurations may be utilized. As demonstrated in FIG. 3, the straps will be positioned in such a position that external compression of the cubital tunnel from the straps is minimized. There will be no brace material in contact with the medial aspect of the elbow, allowing for the irritated ulnar nerve to recover without any potential external forces of compression. The elastic nature of the straps will allow for the patient to adjust the tightness of the brace by applying more force to the strap prior to attaching it to the brace with the hook-and-loop fastener strips.

Components labeled 5 demonstrate two hook-and-loop fastener strips which will be secured via glue or sewn into the brace's straps and used to secure the body of the brace, as well as flexion blocking ball enclosed in the pouch to the arm of the patient. The strips will allow for each strap to be wrapped around the arm of the patient and secured to the brace, preventing the brace from sliding on the patient's extremity to ensure that the flexion blocking ball remains centered in the antecubital fossa. Alternative fastening mechanisms such as buttons and clamps may also be utilized.

In an alternative embodiment, the hook-and-loop fastener strips can be replaced with elastic sleeves that are biased to stay wrapped around the arm of the patient so that the brace will not slide on the patient's extremity and maintain correct placement of the ball. In yet another embodiment, the proximal and distal elastic loops can be replaced with a continuous elastic sleeve or separate elastic straps.

Component 6 demonstrates the inflatable flexion blocking ball. This ball will be placed within the pouch and will serve as a flexion-blocking device, preventing the elbow from flexing past 90 degrees. The ball will have an air valve hole which will allow for inflation using a standard ball inflation needle. Inflating the ball to increasing pressures will provide a progressively higher flexion-blocking force. Patients may tailor the level of inflation to their specific needs and comfort requirements. If the ball is too large or provides insufficient resistance to flexion, the patient may replace it with a tennis ball or similar object to provide increased resistance to elbow flexion. The ball may be made of rubber, foam, plastics, cloth or other materials, and does not necessarily need to be inflatable. The ball may also be substituted for other flexion blocking objects. For example, the ball may be replaced with a foam tube or a set of foam tubes of varying outer diameter or compressibility. Like the ball, the foam tubes can be inserted into the pouch. The flexion blocking object can be inflatable, solid or a combination of both. For example, a combination flexion blocking object can be in the form of a rigid or flexible tube that is encased within an inflatable tube. In another embodiment, the object can be a bilayer object with one layer inflatable and the other non-inflatable (e.g., rigid or flexible).

The flexion object can be in the shape of almost any shape, for example, a sphere, cylinder, cube, diamond, or pyramid. The object can further be shaped on its surface to match the anatomy of the body part to which it will engage.

For example, if the object is a tube, the tube can be shaped to have a first concave portion that mates with the forearm and a second concave portion that mates with the bicep. One function of such concave surfaces is to more comfortably and securely engage the object with the patients anatomy and thereby prevent dislodging of the object from the joint.

The flexion blocking object, whether in the form of a ball or other shape, may be built into or otherwise incorporated into the body of the brace in a manner so that the object is not removable or not easily removable. In one embodiment, the flexion blocking object is held in a fixed position within the enclosure of the brace (i.e., not removable) and adjustments to the object are made only through inflating or deflating the object.

In another embodiment, the flexion blocking object could consist of a combination of inflatable chambers which could be inflated or deflated individually based on the desired resistance to elbow flexion.

Figure 4:
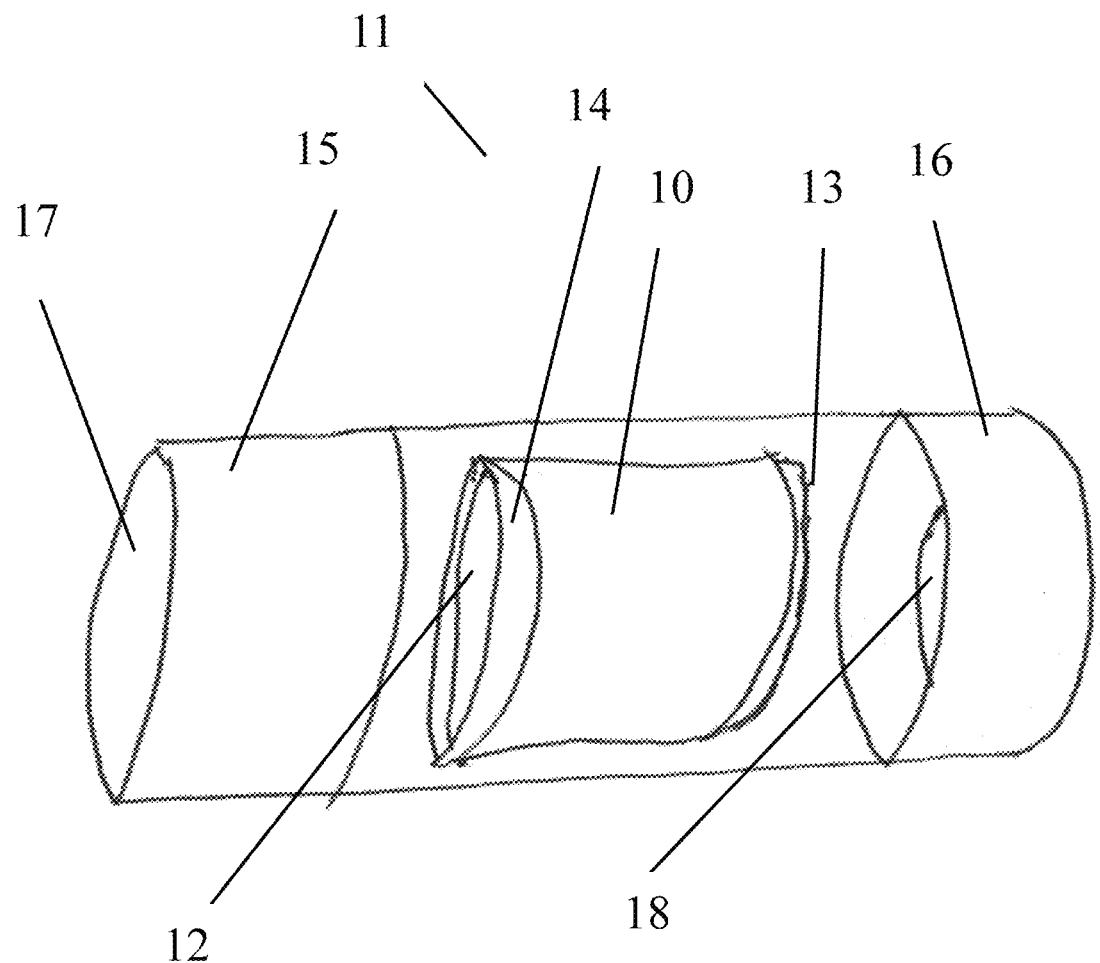
FIG. 4 is a top view of a flexion blocking elbow brace with elastic straps through which the user passes arms and elastic strips to reduce the size of the opening into the pouch.

FIG. 4 illustrates an embodiment in which a pouch 10 on a brace 11 has two openings, 12 and 13, into which an object can be inserted. Either of the two openings 12, 13 can include an elastic strip 14 to reduce the size of the opening into the pouch. The brace 11 also has two elastic sleeves 15, 16 instead of loops. The two elastic sleeves 15, 16 each include openings 17, 18, respectively, that are each configured to receive and enclose a portion of the arm of the patient wearing the brace.

Although the description above is generally directed to the elbow joint, the disclosure is also applicable to almost any joint in the human body, or, for veterinary uses in the animal body. Examples of such suitable joints in which versions of the brace incorporating a solid or inflatable object as described herein may be utilized to restrict motion of joints include the foot, ankle, knee, hip, fingers, wrist, elbow, shoulder, lumbar spine, thoracic spine, and cervical spine.

While a particular form of the invention has been illustrated and described, it will be apparent that various modifications and combinations of the invention detailed in the text and drawings can be made without departing from the spirit and scope of the invention. For example, references to materials of construction, methods of construction, specific dimensions, shapes, utilities or applications are also not intended to be limiting in any manner and other materials and dimensions could be substituted and remain within the spirit and scope of the invention. Other static and adjustable flexion-blocking inserts not described in the above text may be utilized to provide a similar flexion-blocking effect.

What is claimed is:

1. A brace configured to be mounted around an elbow of a patient and one or more objects configured for use with the brace, the brace comprising:
   a distal mounting portion comprising a first loop configured to enclose a portion of an arm of the patient wearing the brace at a region distal to the elbow;
   a proximal mounting portion comprising a second loop configured to enclose a portion of the arm of the patient wearing the brace at a region proximal to the elbow; and
   a body portion positioned between, and connected to, the distal mounting portion and the proximal mounting portion, wherein the body portion includes at least two layers defining a pouch region between the two layers and configured to receive at least one of the one or more objects, wherein the one or more objects are in the shape of a ball, sphere or cylinder,
   wherein the one or more objects are sized to limit flexion of the elbow of the patient beyond about 90 degrees but permit flexion less than about 90 degrees when at least one of the one or more objects are inserted within the pouch region.

2. The brace of claim 1, wherein the object has the shape of a ball.

3. The brace of claim 1, wherein the object is inflatable.

4. The brace of claim 1, wherein the object has the shape of a cylinder.

5. The brace of claim 1, wherein the distal mounting portion includes a first fastener to attach a portion of the first loop to the distal mounting portion and the proximal mounting portion includes a second fastener to attach a portion of the second loop to the proximal mounting portion.

6. The brace of claim 5, wherein each fastener comprises a hook-and-loop fastener strip.

7. The brace of claim 1, wherein the pouch region comprises four sides and three of the four sides comprise the two layers being attached.

8. The brace of claim 7, wherein the fourth of the four sides includes a hook-and-loop fastener to attach the two layers or a button or snap to attach the two layers.

9. The brace of claim 7, wherein the fourth of the four sides includes an elastic strip to reduce the size of the opening into the pouch region.

10. The brace of claim 1, wherein the pouch region comprises four sides and two of the four sides comprise the two layers being attached.

11. The brace of claim 10, wherein two of the four sides are not attached and each includes an elastic strip to reduce the size of the opening into the pouch region.

12. The brace of claim 1, wherein the first loop comprises an elastic sleeve and the second loop comprises an elastic sleeve.

13. A method of treating cubital tunnel syndrome resulting from ulnar nerve compression at the elbow, the method comprising:
    positioning the brace of claim 1 on an arm of a patient with the first loop of the distal mounting portion placed around a distal portion of the arm distal to the elbow and the second loop of the proximal mounting portion placed around a proximal portion of the arm proximal to the elbow; and
    inserting an object into the pouch region of the brace, wherein the object limits flexion of the arm.

14. The method of treating cubital tunnel syndrome of claim 13, wherein the object has the shape of a ball or a cylinder.

15. The method of treating cubital tunnel syndrome of claim 14, wherein the ball or cylinder is inflatable.

16. A method of treating cubital tunnel syndrome resulting from ulnar nerve compression at the elbow by limiting flexion of the elbow of a patient having cubital tunnel syndrome during the period when the patient is asleep, the method comprising:
    providing a brace configured to be mounted around an elbow of a patient, the brace comprising:
       a distal mounting portion comprising a first loop configured to enclose a portion of an arm of the patient wearing the brace at a region distal to the elbow,
       a proximal mounting portion comprising a second loop configured to enclose a portion of the arm of the patient wearing the brace at a region proximal to the elbow, and
       a body portion positioned between, and connected to, the distal mounting portion and the proximal mounting portion, wherein the body portion includes at least two layers defining a pouch region between the two layers and configured to receive at least one or more objects;

providing the one or more objects, wherein the one or more objects are in the shape of a ball, sphere or cylinder or combination thereof;

prior to the patient going to sleep, positioning the brace on an arm of the patient with the first loop of the distal mounting portion placed around a distal portion of the arm distal to the elbow and the second loop of the proximal mounting portion placed around a proximal portion of the arm proximal to the elbow; and inserting at least one of the one or more object into the pouch of the brace, wherein the one or more objects are sized to limit flexion of the elbow of the patient beyond about 90 degrees but permit flexion less than about 90 degrees when at least one of the one or more objects are inserted within the pouch region.

\* \* \* \* \*